US007002161B2

(12) United States Patent
Greene

(10) Patent No.: US 7,002,161 B2
(45) Date of Patent: Feb. 21, 2006

(54) TREATED WATER DISPENSING SYSTEM

(76) Inventor: Ralph G. Greene, 3600 Lee Pike, Soddy Daisy, TN (US) 37379

( * ) Notice: Subject to any disclaimer, the term of this patent is extended or adjusted under 35 U.S.C. 154(b) by 0 days.

(21) Appl. No.: 10/760,641

(22) Filed: Jan. 20, 2004

(65) Prior Publication Data

US 2005/0156119 A1    Jul. 21, 2005

(51) Int. Cl.
*A61L 2/10*    (2006.01)
(52) U.S. Cl. .................. 250/436; 250/435; 422/24; 210/94; 210/97
(58) Field of Classification Search ................ 250/436, 250/435, 434, 432 R; 422/22, 24; 210/94, 210/97
See application file for complete search history.

(56) References Cited

U.S. PATENT DOCUMENTS 6,139,726 A * 10/2000 Greene ..................... 210/94
6,207,046 B1 * 3/2001 Yamashita et al. .......... 210/138
6,648,174 B1 * 11/2003 Greene ....................... 222/66

* cited by examiner

*Primary Examiner*—Kiet T. Nguyen
(74) *Attorney, Agent, or Firm*—Stephen J. Stark; Miller & Martin PLLC

(57) ABSTRACT

A water treatment tank for use with water purification apparatus including an ultra-violet lamp within an encapsulating sleeve onto which incoming water is directed to provide a thin laminar flow about the bulb. The lower compartment has cooling coils about the walls for cooling the water therein relative to the water in the upper compartment. A surrounding sleeve may be located intermediate the encapsulating sleeve and an outer vessel in the tank. A leak detector is located in the encapsulating sleeve. The leak detector and outer vessel are believed to provide safety to users in the event of internal breakage in the tank. A reflective surface is also utilized to direct UV light into portions of the faucets formerly obscured from UV treatment. The faucets preferably provide self-sanitizing capability and an information center selectively displays time until next service, cost savings over bottled water and information related to the dispenser.

19 Claims, 3 Drawing Sheets

TREATED WATER DISPENSING SYSTEM

BACKGROUND OF THE INVENTION

Water purification devices which purify at slow rate, such as those which use the distillation and the reverse-osmosis processes, deliver water into a storage tank or reservoir from which the water is dispensed. The same is true in regard to systems which use bottled water and water filter dispensing coolers. The water, however, may be easily contaminated with bacteria by contact with air on the storage and dispensing mechanisms, or merely by sitting stagnant in the reservoir. This is particularly true with bottled water cooler dispensers and those units that are used as replacements for bottled water cooler dispensers since the tanks are non-pressurized, and therefore must be vented to permit water to be dispensed by gravity flow.

A known method for eliminating bacterial contamination is the use of ultra-violet ("UV") light. The light energy from a UV lamp is germicidal, because UV light penetrates microbial organism's protective membrane layer and photochemically damages the DNA structure, disabling its self-reproducing capability and rendering the cell lifeless.

UV light is in the region of the electromagnetic spectrum that lies between visible light and X-rays. The ultra-violet spectrum ranges from 100 nm to 400 nm wave lengths, with the optimum effective range between 250 nm to 270 nm. The UV lamp is commonly housed in a protective sleeve of quartz which is similar to a test tube that allows ultra-violet transmission and separates the lamp and wiring from the water surrounding the lamp. The quartz sleeve also helps the UV lamp to maintain its optimal operating temperature of approximately 105° F. Factors that determine a UV system's effectiveness include the intensity of the lamp, the exposure time of the water to the ultra-violet rays and the water transmission rate which is determined by the quality and color of the water.

The typical storage reservoir for water purification units is not usually suitable for effective UV application. In gravity-filled storage reservoirs, there must be a method for controlling the water level within the reservoir, and typically a float valve or switch is used. With a UV bulb inside the reservoir, a float valve or switch would normally act as an obstruction to the UV light rays, and provide a sheltered location for bacterial contamination to grow. A typical size and storage capacity for a point of use reservoir is in the order of approximately 4 to 6 gallons, which is required to compensate for the slow recovery rate of the purification system.

Since UV has a limited effective transmission distance, the physical dimensions of a 4 to 6 gallon storage reservoir have not been suitable for effective UV application. A very high intensity UV lamp would be required in such cases and this would heat the chilled water thereby reducing the efficiency and effectiveness of the chilling process. Moreover, UV degrades most plastics, and typically in large reservoirs, floats and switches are constructed of plastic.

A typical point of use and bottled water dispenser reservoir is divided into two compartments by an internal baffle that separates the water which has been cooled from the water that is still at room temperature. Two faucets are used, one for dispensing room temperature water and the other for dispensing chilled water. The baffle that separates the cold and room temperature sections blocks UV rays from reaching one of the compartments in such systems.

It has been observed in U.S. Pat. No. 6,139,726 that the known prior art has not solved any of these problems.

Although U.S. Pat. No. 6,139,726 is a large improvement over the prior art, there still remains a need to reduce the cycling on and off of the UV bulb as well as the "on" time of the bulb as these factors degrade the life of the bulb. Co-pending U.S. application Ser. No. 10/000,874, incorporated herein by reference, addresses this issue and others.

However, even with these improvements, there sometimes exists a need to utilize a larger wattage of UV lamp. Furthermore, a longer bulb would also provide a longer exposure time with thin film flow around the UV lamp and the quartz sleeve. A need exists to provide UV energy to areas previously inaccessible to the UV rays. A need also exists to detect leaks into the quartz sleeve about the UV lamp. Furthermore, a need exists to provide protection to a user in the event of breakage of a sleeve and/or lamp.

SUMMARY OF THE INVENTION

Consequently, it is a primary object of the present invention to provide a water dispensing system for dispensing at lease one of room temperature and chilled water which has been treated and purified by an ultraviolet source.

It is another object of the present invention to provide a water treatment tank having an ultraviolet energy source therein for effectively decontaminating at least one room temperature and chilled water which may be contained therein, the tank receiving water from a clean water source such as a distillation/condensation purifier, a point of use filtration source, a reverse osmosis purifier or a bottled water source.

It is a further object of the present invention to provide a water dispensing system including a treatment tank having an ultraviolet (UV) energy source in the form of a lamp for purifying the water therein, the water directed on the UV lamp in a laminar flow fashion with a reflector directing UV energy toward a dispensing portion of the system.

It is a still further object of the present invention to provide a water dispensing system including the treatment tank having an ultraviolet (UV) energy source in the form of a lamp for purifying the water therein, the water being exposed to UV rays while being added to the tank and periodically when not dispensing water from the tank, and while in portions of the outlets.

It is another object of the present invention to provide a water dispensing system including a treatment tank having an ultraviolet (UV) energy source in the form of a lamp contained in an encapsulating tube with a leak detector located in the tube.

Another object of the present invention is to provide a water dispensing system including a treatment tank having an ultraviolet energy source in the form of a lamp with an outer vessel surrounding and then containing at least a portion of the lamp in the event of lamp and/or sleeve breakage.

It is a further object of the present invention to provide a leak detector proximate to the lamp which provides a signal to shut a solenoid operated valve to secure operation of the water dispensing system.

It is a still further object of the present invention to provide a water dispensing system including a treatment tank having a reflective surface which at least partially directs UV energy to otherwise obscured areas.

It is an object of the present invention to provide a dispenser that can display a number of days to service based on a daily usage level and a rated gallons of the limiting design components such as a filter or UV bulb.

It is an object of the present invention to provide an information center with a display to provide information to a consumer about the water filter purification system and/or filter utilized with the dispenser.

Another object of the present invention is to provide an updated display providing the amount of money saved by utilizing the dispenser over the cost of buying bottled water.

Another object of the present invention is to provide a self-sanitizing faucet which advantageously and periodically sanitizes water contained within the faucet to prevent contamination by bacteria or other contaminants.

Accordingly, the present invention provides a water dispensing system wherein water is treated by ultraviolet rays in a treatment tank to purify the water prior to being dispensed. Water entering into the treatment tank is directed so that it is channeled onto the UV lamp where it flows about the sleeve of the lamp in a thin film greatly increasing the ultraviolet exposure so that a low energy lamp may be effective even under full flow conditions. The lid of the tank may be extended to allow for a longer, and possibly, a larger wattage UV lamp. A reflector may be placed along the lid, which directs at least some of the UV light towards areas which would otherwise be obscured, such as within the outlet waterways.

An enclosing sleeve, or encapsulating tube, about the UV lamp maintains a moisture-free environment about the UV lamp. A leak detector is preferably located in the enclosing sleeve. An outer vessel extends about the enclosing sleeve. An outer vessel extends about the enclosing sleeve and/or surrounding sleeve to catch the sleeve(s) and/or lamp in the event of breakage. The leak detector provides a signal to the inlet valve to shut off the system in the event of breakage to prevent sleeve or lamp materials from being carried into the tank.

The treatment tank may have separating baffle which separates room temperature water from chilled water and the ultraviolet lamp extends into both compartments. Moreover, a transparent tube preferably formed from polytetrafluoroethylene or the like extends through the chilled water compartment below the baffle and communicates the room temperature water with the outlet faucet therefor. The water in the tube is thus radiated by the ultraviolet light emanating from the bulb while the room temperature water is within the tube waiting to be dispensed.

The dispenser also employs the use of information center which can provide a days until service display, as well as an information display showing the type of water purification system employed. Furthermore, the information center can display the amount of savings from using the dispenser as opposed to the cost of buying bottled water.

Furthermore, the preferred dispenser utilizes self-sanitizing faucets which provide an ability to elevate portions of the faucet to pre-determined temperatures for pre-determined periods of time in order to kill bacteria or other contaminants.

BRIEF DESCRIPTION OF THE DRAWINGS

The particular features and advantages of the invention as well as other objects will become apparent from the following description taken in connection with the accompanying drawing in which.

DESCRIPTION OF THE PREFERRED EMBODIMENT

Figure 1:
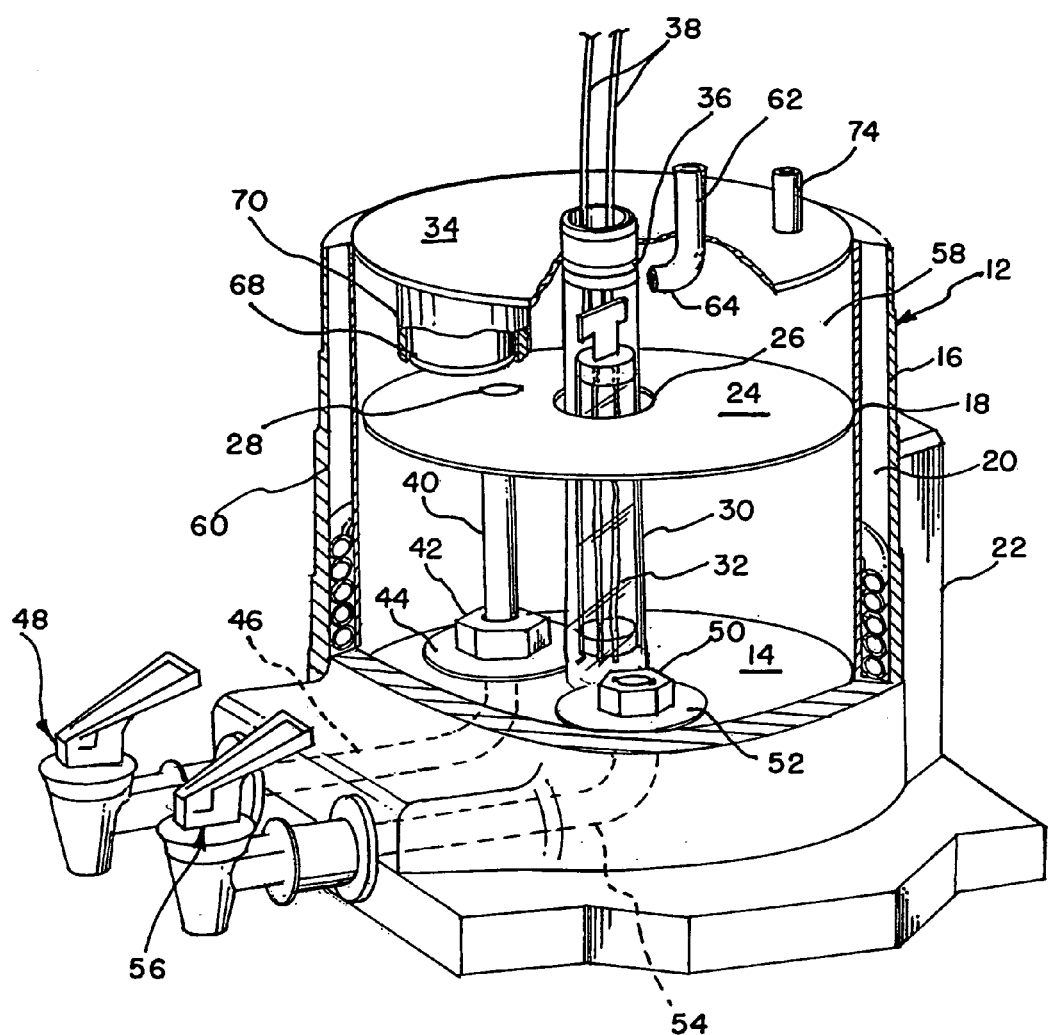
FIG. 1 is a prior art cooler.

Referring now to the drawing FIG. 1 illustrates a prior art water dispenser 10. The dispenser 10 includes a housing 12 having a hollow interior including a base 14 and an exterior upstanding wall 16. In at least the lower portion of the housing above the base spaced inwardly from the wall 16 is a second wall 18. Tubing forming cooling coils 20 are received in a coiled condition between the walls 16 and 18, the coils 20 carrying coolant communicating with refrigeration apparatus (not illustrated) mounted within a bulbous portion 22 of the housing 12 preferably externally of the wall 16 for reasons which will hereinafter become clear.

Fastened to the interior wall 18 within the hollow interior of the dispenser is a baffle plate 24, the baffle plate preferably being constructed from stainless steel and having a substantially central opening 26 and a smaller offset opening 28. Extending downwardly through the opening 26 and having portions disposed both above and below the baffle 24 is an outer bulb 30, or tube, in which an ultraviolet lamp 132 is mounted, the bulb being a conventional fused quartz bulb such as a test tube. The bulb 30 extends through an upper lid 34 which covers and closes the hollow interior of the dispenser and the bulb is closed at the upper end by a seal or grommet or other closure member 36 through which electrical conductors 38 pass outwardly to an electrical source (not illustrated).

Also extending through the baffle plate 24 is a transparent tube 40 which preferably is formed from polytetrafluoroethylene sold under the trademark TEFLON (TM). The tube 40 permits UV rays to pass therethrough and is not deteriorated by these rays. The tube 40 extends into and through a nut 42 and through a washer 44 beneath the nut into the base where it communicates through tubing 46 connected to the nut 40 with a manually operable faucet valve 48. Another nut 50 positioned on a washer 52 communicates through tubing 54 with another manually operable faucet valve 56.

The baffle plate 24, if utilized, divides the interior of the dispenser 10 into an upper compartment 58 and a lower compartment 60. The baffle plate could be Teflon(™), stainless steel or other appropriate material. Transparent and/or translucent baffle plates are not believed to be known in the art. Secured to the lid 34 and extending into the upper compartment 58 is a water supply tube 62 which may be connected to a source of potable water, which may be filtered water or bottled water. The end of the tube 62 within the dispenser is bent or angled at 64 so that the water 66 exiting the tube 62 is directed onto the bulb 30 about the ultraviolet lamp 132 which provides a thin film laminar flow about the bulb as described in U.S. Pat. No. 6,139,726. This permits use of a low wattage ultra-violet lamp and also insures that all of the water entering the dispenser is treated by the UV light rays.

Mounted within the upper chamber 58 carried by the lid 54 is a float switch 68 mounted within a shield 70. As is the case with the baffle 24, the shield 70 and the nuts 42, 50 and washers 44, 52 are constructed from stainless steel or other UV resistant material so as not to be affected by the ultra-violet rays. A vent tube 74 opening outwardly of the dispenser communicates air to the dispenser so that the water within the dispenser may flow by gravity. The lid 54 may also have a seal instead of, or in addition to, the vent tube 74 that prevents contaminants from getting into the reservoir and forcing air through an air filter that removes airborne contaminants.

As described, all of the elements within the dispenser 10 are typically constructed from quartz, stainless steel or TEFLON (TM) which do not deteriorate as a result of the ultra-violet rays of the lamp 132. Moreover, the room temperature water within the upper compartment 58 communicates with the manually operable dispensing valve or faucet 48 through the tube 40 within which this water sits prior to opening of the valve 48. Thus, UV rays act on the water within the tube 40 while the water is in the tube and as the water flows therethrough, thereby insuring that the water remains substantially free of bacteria and effectively pure until the water has exited the dispenser. The water within the lower compartment 60 is chilled by the cooling coils 20 and remains substantially pure until dispensed through the dispensing valve 56. Furthermore, by placing the float switch 68 within a stainless steel shield so that it need not be outside of the dispenser, the water may enter the dispenser directly for fast refill, and by channeling or directing the incoming water directly on to the UV lamp bulb so that it may flow around and contact substantially the entire surface of the bulb in a laminar thin film, the exposure of the water to UV rays is greatly increased even during fast refill and dispensing. This aids in permitting a low wattage UV lamp and reduces the cooling refrigeration requirements for the cooled water.

Figure 2:
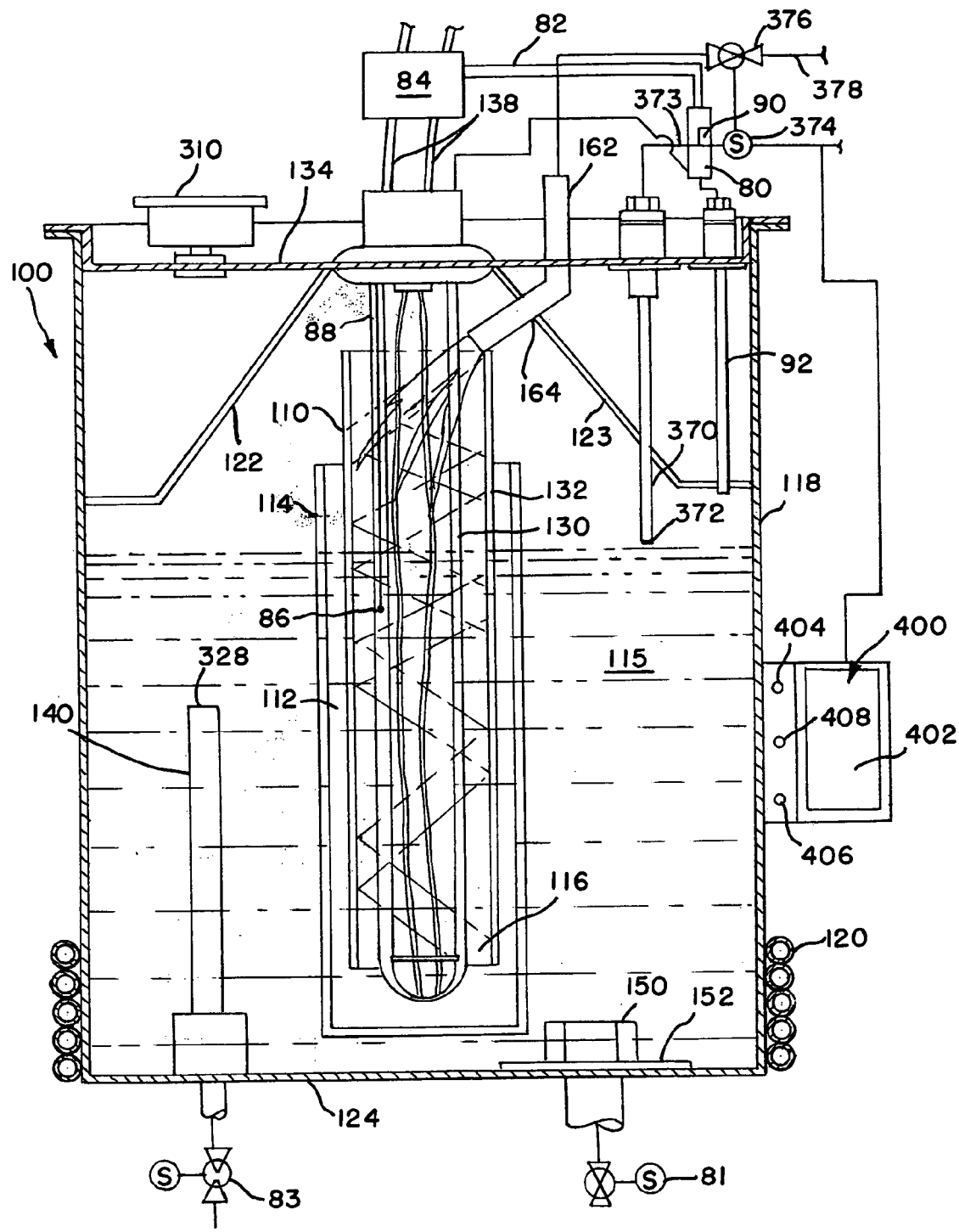
FIG. 2 is a perspective view partly broken away and sectioned of a water dispenser constructed in accordance with the principles of the present invention.
Figure 3:
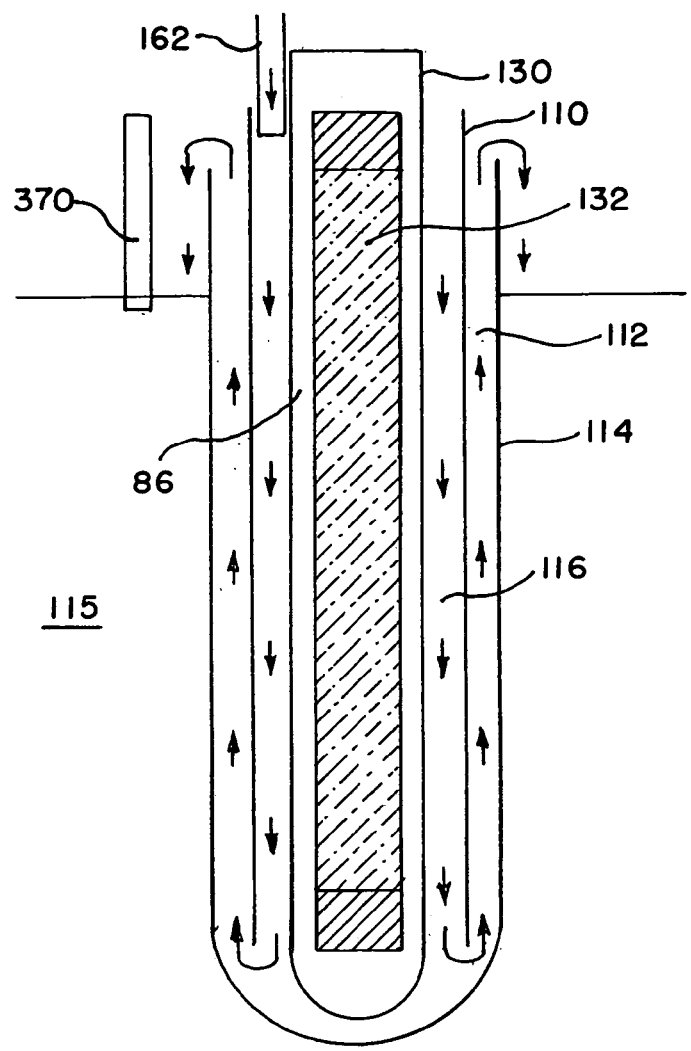
FIG. 3 is a detailed view of the flow of water into the tank past a UV lamp in an alternatively preferred embodiment.

FIG. 2 shows the preferred embodiment of the present invention without the baffle plate 24. Of course, the baffle plate 24 could be utilized if desired in some embodiments. Here, the water entering the dispenser 100 again enters through the bent portion 164 of the tube 162 and is directed onto the sleeve 130, or tube, disposed about the ultra-violet lamp 132 to provide a thin laminar flow of water, preferably 360 degrees, to treat the incoming water with UV light rays.

The level of the water within the dispenser 100 should be above the upper open end 328 of the tube 140 in order to dispense room temperature water. This may be accomplished by using a first probe 370 fastened to the lid 134 and projecting downwardly into the dispenser tank. The first probe 370 is preferably located along the wall 118 to prevent water from being located behind the probe 370 avoiding treatment by the lamp 132. The first probe 370 may be a stainless steel member having an electrical conductivity sensing device 372 at its tip which is within the dispenser 100 which detects when the water is at the level of the tip. The output of the first probe 370 is connected electrically by conductors 373 to a controller 80 connected to a normally closed solenoid 374 of a solenoid valve 376 which is mounted in the water line 378 between a source of water and the tube 162. When the water level within the dispenser tank falls below the tip of the first probe 370, a signal is received by the controller 80.

The controller 80 is illustrated as an electronic component having at least a limited processor configured to receive inputs from at least one probe, and preferably a timer 90, and provide output signals to the valve solenoid 374 and the switch 84. This results in a signal being sent through the conductor 82 to switch 84 to activate the UV lamp 132, since the lamp 132 is normally not activated as the switch 84 is normally in the off position.

After being activated, the lamp 132 reaches a desired operating temperature. Whether the lamp has reached the desired operating temperature may be evaluated by the controller 80 using a temperature measuring device located within the tube 130 and connected by conductor to the controller 80, or by the passing of a predetermined amount of time from the activation of the lamp 132 as measured by a timer 90 which may be a part of the controller 80. Of course, the temperature measuring device 86 is illustrated above the anticipated high water level to avoid obscuring portions of the tank from treatment. Upon reaching the desired operating temperature, the controller 80 sends a signal to the solenoid 374 to open valve 376 to begin filling the dispenser.

When the water reaches the level of the first probe 370 or float switch, the controller 80 will be aware that the minimum water level has been restored in the dispenser 100. However, in order to minimize the cycling of the UV lamp 132 on and off, a second probe 92 may be fastened to the lid 34 and projects downwardly into the dispenser tank. The second probe 92 is preferably similarly constructed to the first probe 370, except that the probe tip does not extend as deeply into the tank as the first probe 370. The second probe 92 may also be located against the wall 118 to avoid creating areas which are not treated by the lamp 132. Alternatively, instead of relying on the second probe 92 or possibly even utilizing a second probe 92, the passing of a predetermined time from point of contact with the first probe 370 may be utilized to shut off the solenoid 374 and close the valve 376. A restriction valve may be utilized on the water supply to ensure a regulated flow rate into the tank. The flow restrictor can prevent incoming flow from overfilling the reservoir. If the second probe 92 is not triggered in a predetermined amount of time, the controller switches off the solenoid valve 376 since there is obviously a leak in the tank. Furthermore, if the first probe 370 does not detect water in a predetermined amount of time, a leak condition may also exist and the valve 376 may be switched off.

The controller 80 is useful in detecting leaks from the water dispenser 10 in the preferred embodiment. In a case where water is leaking from a faucet 48,56 at full flow, the solenoid valve 376 would normally open and remain open because the reservoir could not refill. To detect this leak, the controller 80 preferably only allows the solenoid valve 376 to open for a maximum time limit. If the time limit is exceeded, the solenoid valve 376 will be closed by the controller 80 and an alarm would be activated to let the user know that a leak may have been detected. Water from these dispensers 10 is not dispensed continually, but dispensed on-demand when needed by the user. Water is usually dispensed periodically and at varying amounts so that continuous flow past a preset limit would not be a normal condition for a water dispenser 10 of the preferred embodiment.

When the solenoid valve 376 opens to refill the reservoir in tank 115, the valve 376 opens fully and the water flows at a rate based on the water pressure and the restrictions within the water lines and solenoid valve 376. In general terms, if a 12-ounce cup of water is drawn from the reservoir 115, the amount of time required with the solenoid valve 376 to open to refill the 12-ounce volume will be constantly within some tolerance level. Leaks within the reservoir 115 or faucets 48,56 at less than full flow, even down to a drip leak will create a pattern of time that it takes to refill the reservoir 115 and a pattern of time that it takes for the water level to drop enough to activate the solenoid valve 376 to open. The controller 80 logs the "open" time interval and the "closed" time intervals. The "open" and "closed" intervals (within a certain range) repeat, a set number of times, the controller 80 will activate an alarm mode and will not open the solenoid valve 376 again until the alarm mode has been de-activated by the user. The "repeat" pattern number can be as little as two or greater than five based on the performance desired.

When the water reaches the desired level such as the level of the second probe 92, if utilized, a signal is sent to the controller 80. The controller then sends a signal to the solenoid 374 to close the valve 376. The switch 84 may then be turned "off" to deactivate lamp 132 after a first predetermined time. The distance between the tip of the first and second probes 370, 92 is anticipated to hold a sufficient volume of water to reduce the cycling of the UV lamp 132 on and off. In the preferred embodiment, this volume would be about sixteen ounces, or about four cups of about four ounces of water. It is estimated that the number of lamp starts could be reduced up to about 80% thereby reducing the energy consumption of the dispenser and extending the life of the lamp 132.

In the preferred embodiment, an information center 400 is mounted to the wall 118 or other appropriate location on the dispenser 100. The information center 400 is utilized to convey information about the dispenser 100. In fact, the information center 400 could be utilized with a UV type dispenser 100 as shown along with any type of water filtration or purification system known in the art.

The information center 400 is illustrated connected to the controller 80 and/or solenoid valve 83,81 such that the information center 400 can calculate and/or display the number of days to service the dispenser 100. To calculate the number of days to service, the average daily usage of the dispenser 100 is calculated. A total amount of water dispensed may be subtracted from the rated life of the filter and/or purification method such as a lamp life of the UV bulb. The remaining life is then divided by the average daily usage to provide an anticipated number of days of service. This number may be displayed on the display 402 by pressing a status button 404 which initiates this calculation or otherwise provided. Average daily use of the filter system may be calculated by determining the amount of water dispensed. Information can be obtained as from the controller 80, or from solenoid valves 81,83 or 376. Time since the last service can be reset just by resetting the controller 80 or other appropriate component to reset the information center 400 upon completion of a service. Other methods can also be utilized to provide a number of days until next service.

In the preferred embodiment of the information center 400, a second display can be provided on the screen 402 such as by pushing the second button 406. Water treatment information may then be displayed on the screen 402. The display can identify the type of filter or filters and/or purification means such as ultraviolet light, the wattage of the bulb or other pertinent information related to the type of water filtration provided by the dispenser 100. This could assist in informing a consumer about how the water has been treated that they have dispensed or are about to dispense from the dispenser 100.

Additionally, the information center 400 may be utilized to provide an estimated cost savings display on the screen 402. In the preferred embodiment, the third button 408 provides a signal to the information center 400 to calculate this savings. First, the cost of bottled water may be calculated and displayed based on a local regional and/or national cost of bottled water. Presently, it may be $1.00 or more per gallon. The total cost of bottled water in five-gallon containers or otherwise is dispensed through a cooler usually has a monthly cooler rental fee as well as a per-gallon cost of delivered water and the sales tax on the cost of bottled water. Accordingly, the average cost per gallon may be calculated.

Next, the cost of the point of use system may be calculated as a monthly fee. By determining the amount of water dispensed by the dispenser 100 such as by the determined amount of water passing through any of the solenoid valves 83,81, or 376, the combination of the solenoid valves 83,81 or the solenoid valve 376, or alternatively calculated by a controller 80 or other means, the amount of water passing through dispenser 100 may be calculated on a per-gallon basis and displayed relative to the local market price per gallon of bottled water on the screen 402. Savings may be displayed in several views such as a total cost over the life of the dispenser such as by calculating the total amount of water dispensed and the total number of days in service. Next, the difference in cost of the rental rates of the bottled water cooler and the point of view system could be calculated. This sum could either be added or subtracted from the per-gallon cost of the bottled water usage to provide a total cost savings on the screen 402. A savings per amount dispensed, per gallon or other view could also be provided.

Inside the encapsulating tube 130 is preferably located a leak detector such as electrode 86. The electrode is connected by connector 88 to the controller 80 so that in the event electrode 86 detects the presence of water in the encapsulating tube 130, the valve 374 may be shut off until the leak into the encapsulating tube 130 has been corrected. This also ensures that broken sleeves and lamp portions are not carried into the tank volume 115. The controller 80 may also shut off flow out of the tank through use of solenoid valves 81 and 83 upon the receipt of a signal from the leak detector. The electrical probe 86 detects if water has entered the encapsulating tube 130 so that none of the tube 130 or lamp 132 is carried into the tank volume 115 in the event of breakage (i.e., so that a user of the system 10 does not inadvertently dispense contaminated water from the tank, which may possibly contain sharp shreds from a broken lamp and/or sleeve or possibly mercury from a broken lamp). Ground fault interrupters (GRI's), fuse systems, or other appropriate devices known in the art may also be utilized as a portion of or with leak detectors.

A surrounding sleeve 110 may be utilized by some embodiments to force the laminar flow downwardly 360° about the tube 130 and then back up intermediate gap 112 created between the surrounding sleeve 110 and outer vessel 114 so that water can then spill over laminally the edge of outer vessel 114 flowing in a thin film downward and into the volume of the tank 118. This retains incoming fluid proximate to the lamp 132 for an extended distance and time duration. Furthermore, the surrounding sleeve 110 preferably extends a distance above the outer vessel 114 so that laminar flow may occur at least above the height of the outer vessel 114. The top of the outer vessel 114 is preferably located above the tip 372 of probe 370 and above the tip of probe 92.

The outer vessel 114 is preferably made of a transparent, non-breakable material such as TEFLON (TM) which prevents the quartz sleeve 110 and/or encapsulating tube 130 or lamp 132 materials from falling into the tank 118 in the event of breakage and also allows the UV rays to continue penetrating into water external to the outer vessel. The outer vessel 114 also generates laminar flow as water spills over into the tank volume 115. The outer vessel 114 may have a round, pointed, or other shaped base below the lamp 132 and/or sleeve 110.

The encapsulating tube 130 is preferably non-vented so that moisture from air does not condense inside the tube 130 thereby possibly contacting the leak detector 86 and triggering an alarm condition.

Also, shown in phantom is a spiral tube 116 which may be utilized in some embodiments to slowly and methodically provide water about the lamp 132. While not utilized in the presently preferred embodiment, this feature could be advantageous in other embodiments.

Finally, reflective surfaces 122,123 are shown descending from lid 134. The reflective surfaces 122,123 may also be a portion of the lid 134. The reflective surfaces are preferably oriented to direct at least some of the UV light rays into at least portions of the tube 140, cold water outlet 150 and faucet portions of the hot and cold faucets.

Figure 4:
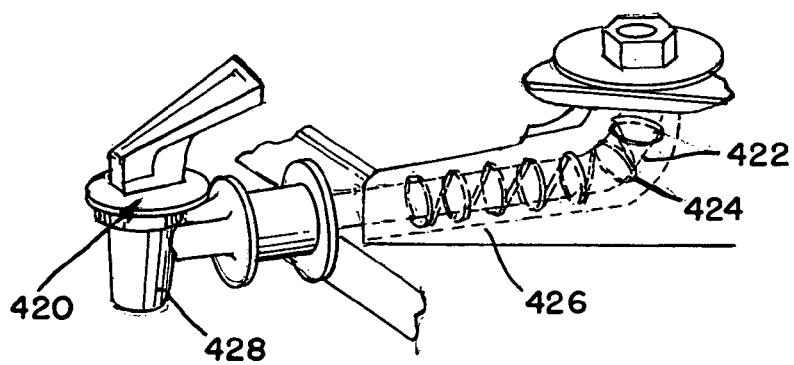
FIG. 4 is an improved faucet design for use with water dispensers including the embodiments of FIGS. 2 and 3.

Although the prior art faucet designs 48,56 can be utilized, FIG. 4 shows an improved and presently preferred faucet design 420. This faucet design is a self-sanitizing water cooling faucet. This is believed to be helpful to prevent contamination by airborne bacteria viruses, or other contaminants. Prior art faucets can be contaminated by hand contact. The preferred faucet 420 employs stainless steel tubing 422 or other appropriate tubing material which can be heated with a heater such as with wrapped wire 424 as shown in FIG. 4. A layer of insulation 426 is useful in containing the wrapped or heated tubing 422 when the temperature is elevated. By utilizing a controller 80 or other appropriate mechanism, the heater illustrated as wire 24 can elevate the temperature of the tubing 422 for a set period of time to or above a desired temperature (such as above 180° F. for a minute). This effectively sanitizes both the faucet and the waterway. Furthermore, this can be utilized to eliminate any potential contamination of the water that is inside the faucet and the waterway.

The heating element 424 can be activated periodically such as every 12 to 24 or even every 48 hours depending on whether protection from contaminants is desired. This can be controlled automatically and electronically such as by the controller 80, information center 400 or otherwise. An in-line shutoff valve such as solenoid valve 81,83 as shown in FIG. 2 can be incorporated with this faucet design. These can close and open water passage through the tubing. As shown in FIG. 4, a housing 428 or other appropriate cover or face plate can protect both hand contamination and prevent the consumer from contacting the tubing 422 or other internal components while the faucet 420 is undergoing the sanitizing cycle.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

What is claimed is:

1. A water dispenser comprising a housing having a water treatment tank, a water inlet selectively feeding water into an upper section of said tank, cooling coils acting to chill water in a lower section of said tank, an ultra-violet lamp disposed in both the upper and lower sections of the tank for transmitting ultra-violet light rays to water in both upper and lower sections to eliminate bacterial growth in both upper and lower sections, an encapsulating sleeve disposed about the ultra-violet lamp providing a water free area about the lamp, a first faucet communicating with said lower section for dispensing chilled water selectively, and a leak detector sensing in the water free area.

2. The water dispenser as recited in claim 1 further comprising a reflective surface located in the upper section of the tank.

3. The water dispenser of claim 2 wherein the reflective surface reflects ultra-violet rays from the lamp into at least a portion of the first faucet.

4. The water dispenser of claim 1 further comprising a solenoid valve in communication with the water inlet wherein when the leak detector detects water in the water free area, the solenoid valve is shut.

5. The water dispenser of claim 1 further comprising an outer vessel disposed in the tank below and around at least a portion of the lamp and encapsulating sleeve.

6. The water dispenser of claim 5 further comprising a surrounding sleeve intermediate the outer vessel and the encapsulating sleeve, said surrounding sleeve spaced to provide an opening intermediate the surrounding sleeve and outer vessel wherein water passes through the opening as it is fed toward the upper section of the tank.

7. The water dispenser as recited in claim 6 further comprising a baffle separating the upper and lower sections of the tank, said baffle connected to the outer vessel.

8. The water dispenser of claim 1 further comprising a translucent baffle separating the upper and lower sections of the tank.

9. A water dispenser comprising a housing having a water treatment tank, a water inlet selectively feeding water into an upper section of said tank, cooling coils acting to chill water in a lower section of said tank, an ultra-violet lamp disposed in both the upper and lower sections of the tank for transmitting ultra-violet light rays to water in both upper and lower sections to eliminate bacterial growth in both upper and lower sections, a first faucet communicating with said lower section for dispensing chilled water selectively, and a reflective surface disposed in an upper portion of the tank reflecting ultra-violet rays into at least a portion of the first faucet.

10. The water dispenser of claim 9 further comprising an encapsulating tube about the ultra-violet lamp, said encapsulating tube providing a water free area about the ultra-violet lamp.

11. The water dispenser of claim 10 further comprising a leak detector sensing in the water free area.

12. A water dispenser comprising a housing having a water treatment tank, a water inlet selectively feeding water into an upper section of said tank, cooling coils acting to chill water in a lower section of said tank, an ultra-violet lamp encapsulated in both the upper and lower sections of the tank for transmitting ultra-violet light rays to water in both upper and lower sections to eliminate bacterial growth in both upper and lower sections, a first faucet communicating with said lower section for dispensing chilled water selectively, a surrounding sleeve spaced from and located about a portion of the ultraviolet lamp, and an outer vessel located below and about a portion of the surrounding sleeve with an opening intermediate the surrounding sleeve and the outer vessel communicating water from the water inlet intermediate the surrounding sleeve and the ultra-violet lamp through the opening and then intermediate the surrounding sleeve and the outer vessel prior to feeding the water into the upper section of said tank in a thin film laminar flow.

13. The water dispenser of claim 12 further comprising a reflective surface in an upper section of the tank.

14. The water dispenser of claim 13 further comprising an encapsulating sleeve about the ultra-violet lamp providing a water free area about the ultra-violet lamp inside the encapsulating sleeve, and water fed from the water inlet passing external to the encapsulating sleeve as it is fed intermediate the surrounding sleeve and the ultra-violet lamp.

15. The water dispenser of claim 14 further comprising a leak detector sensing in the water free area.

16. The water dispenser of claim 15 further comprising a solenoid valve in communication with the water inlet and when the leak detector detects water in the water free area, said solenoid valve is shut.

17. A water dispenser comprising a housing having a water treatment tank, a water inlet selectively feeding water into an upper section of said tank, cooling cold chilled water in the lower section of the tank, and ultra-violet lamp disposed above the upper and lower sections of the tank for transmitting ultra-light rays to water in both upper and lower sections to eliminate bacteria growth in both upper and lower sections, a first faucet communicating with said lower section for dispensing chilled water selectively, and a translucent baffle separating the upper and lower sections of the tank.

18. A water dispenser comprising a housing having a water treatment tank, a water inlet subsequently feeding into an upper section said tank, cooling coils acting to chill water in a lower section of said tank, an ultraviolet lamp disposed in the upper and lower section of the tank for transmitting ultra-violet light rays to water in both upper and lower sections to eliminate bacteria growth in both upper and lower sections, a first faucet communicating with said lower section for dispensing chilled water selectively, a solenoid valve connected to the water inlet; and a controller sensing an open time of the solenoid valve wherein the open time is compared to an expected open time and if the open time exceeds the expected open time, performing one of activating an alarm and closing the solenoid valve.

19. A water dispenser comprising a housing having a water treatment tank, a water inlet selectively feeding water into an upper section of said tank, cooling cold chilled water in the lower section of said tank, an ultra-violet lamp disposed in both the upper and lower sections of the tank for transmitting ultra-light rays to water in both upper and lower sections to eliminate bacteria growth in both upper and lower sections, a first faucet communicating with said lower section for dispensing chilled water selectively, a baffle separating the upper and lower sections of the tank, and an outer vessel located below and about at least a portion of the lamp with said outer vessel connected to the baffle.

* * * * *